United States Patent [19]

Evans et al.

[11] Patent Number: 5,635,579
[45] Date of Patent: Jun. 3, 1997

[54] COMPOSITIONAL ADDITIVE COMPRISING TERPOLYMERIC FLUID

[75] Inventors: Edwin R. Evans, Clifton Park; Gregory H. Slocum, Niskayuna, both of N.Y.

[73] Assignee: General Electric Company, Waterford, N.Y.

[21] Appl. No.: 561,214

[22] Filed: Nov. 21, 1995

Related U.S. Application Data

[63] Continuation of Ser. No. 74,193, Jun. 10, 1993, abandoned.
[51] Int. Cl.⁶ .................................................. C08G 77/04
[52] U.S. Cl. ........................... 528/37; 528/42; 528/43; 528/14; 528/18; 524/263; 556/467
[58] Field of Search .................................. 528/37, 42, 43, 528/14, 18; 524/263; 556/467

[56] References Cited

U.S. PATENT DOCUMENTS

| | | |
|---|---|---|
| 4,089,833 | 5/1978 | Simpson . |
| 4,122,247 | 10/1978 | Evans . |
| 4,157,337 | 6/1979 | Evans ................... 260/448.2 |
| 4,742,101 | 5/1988 | Yoshida . |

FOREIGN PATENT DOCUMENTS

| | | | |
|---|---|---|---|
| 700126 | 12/1964 | Canada ................... 528/37 |
| 0255967 A | 2/1988 | European Pat. Off. . |
| 0384699 A | 8/1990 | European Pat. Off. . |
| 0563902 A | 10/1993 | European Pat. Off. . |

*Primary Examiner*—Helen Lee
*Attorney, Agent, or Firm*—Kenneth S. Wheelock

[57] ABSTRACT

Methyl- and phenyl-containing fluorosilicone terpolymeric fluids over the range of 30 cps to 200,000 cps are effective as additives for various uses. Over the range of 16,000 to 200,000 cps, the fluids are effective as additives in promoting a finger transferable self-bleed of lubricant in fluorosilicone-containing heat-curable rubber compositions, even after a post-bake of the composition. Over the viscosity range of 30 cps to 1000 cps, the fluids are useful in personal care and cosmetic products as water and oil repellency additives. Methods of ring opening polymerization are used to produce the terpolymeric fluids from cyclic reactants.

3 Claims, No Drawings

COMPOSITIONAL ADDITIVE COMPRISING TERPOLYMERIC FLUID

This is a continuation of application(s). Ser. No. 08/074193 filed on Jun. 10, 1993, now abandoned.

BACKGROUND OF THE INVENTION

This invention relates to a fluorosilicone terpolymeric fluid which, at a high viscosity, can be used as a self-bleed additive for fluorosilicone heat curable rubber compositions. More particularly, the present invention relates to a self-bleed additive which acts as a release agent after post baking a fluorosilicone heat curable rubber composition. At a low viscosity, the fluid can be used as an additive for personal care products to enhance the water and oil repellency of the products.

Elastomeric heat curable rubber (HCR) compositions derived from fluorosilicone high molecular weight (HMW) polymers are utilized in applications which require good solvent resistance and good mechanical properties. The cured compounds are often used in applications where a molded part must be inserted into a metal appliance prior to utilization of the molded part. A raw material user, or fabricator, usually works with uncured compositions, injecting them into molds where they are press-cured to form a molded part. Occasionally, the fabricator requires a lubricated surface on a cured part to facilitate insertion of the part into a mechanical appliance of some kind. Most processes avoid the use of externally applied lubricants and instead preferably use compounds which release a film of lubricant to the cured surface after the curing process (press cure and post bake). Compounds which incorporate lubricants and release them after molding are called self-bleed compounds.

It is desired to produce a fluorosilicone heat curable rubber composition which exhibits a self-bleed after post-baking. Such a composition could be used to provide a molded gasket or seal which would exhibit lubricant on its outer surface and would thus easily slip over or into a metal part/appliance despite a tight fit. For example, it is desired to provide a self-bleeding insulator for a spark plug which can easily slip over the plug yet provide a tight fit to the plug.

The fabricator also prefers a self-bleed additive which does not liberate excess volatiles in the post-bake oven. Such volatiles may be environmentally unacceptable and dangerous to the user.

Self-bleed compounds are made by incorporating a non-compatible fluid into an HCR composition in an amount sufficient to effect a "bleed". The utilization of phenyl-containing silicones in this application is well known for polydimethylsiloxane (PDMS). Improving the efficacy of the self-bleed of PDMS by adding fluorosilicone containing fluids is described in European patent application no. 369,255.

The utilization of a phenyl-containing copolymeric fluids as a bleed agent for fluorosilicone compositions has been described in U.S. Pat. No. 4,742,101 to Yoshida. Yoshida discloses that copolymeric fluids where the phenyl group varied over the range of 70/30–25/75 are most effective.

A typical bleed agent formulation disclosed in Yoshida is:

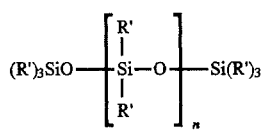

wherein some of the R' groups are phenyl groups and some are methyl groups. Two typical examples are:

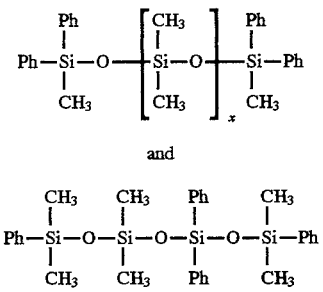

where x=1 or 3, and Ph is a phenyl group.

When used in conjunction with diphenyl diol filler treating agents, these fluids self-bleed after the composition is cured at 165° C. for 10 minutes. In Yoshida, all of the bleeds are described as being good after press cure. However, Yoshida provides no information about the self-bleed performance of the compositions after post bake.

The type of self bleed preferred on the post-bake samples is one which, when handled, allows a user to know there is a lubricant on the surface and wherein the lubricant is transferred to the hands.

One problem with the Yoshida agents is that processability is adversely affected by the addition of phenyl-containing copolymer fluids. These fluids tend to liver-up the material during addition of the fluid to material on a mill. The term "liver-up" has become well known to those of skill in the art and refers to the condition of stock material when it becomes too wet and either becomes too difficult to apply on a mill or falls off the mill. To minimize this problem, it is necessary to add raw fumed silica to soak up the fluid in the composition. The utilization of the fumed silica offsets a decrease in Durometer which often occurs with the addition of the self-bleed fluids.

Fluorosilicone HCR compositions prepared with known phenyl-containing silicone fluids do not perform very well. The bleed of the compositions was erratic. Testing done on compositions utilizing diphenyl diol as described by Yoshida improved the performance of the phenyl-containing silicone fluids in self-bleed after press cure; however, no improvement in performance was exhibited after post bake.

Some of the same desired properties of a self-bleed additive are also desirable in personal care products such as skin creams and lotions, hair conditioners, lipsticks, antiperspirants and deodorants. It is particularly desirable that these products exhibit excellent water and oil repellency and a resistance to washing off.

SUMMARY OF THE INVENTION

The invention is based upon the discovery that a methyl-phenyl-fluoro-silicone terpolymeric fluid can be used as a self-bleed additive at high viscosities and as a personal care additive at low viscosities. At high viscosities, the fluid is useful as an additive for fluorosilicone HCR compositions and enables HCR compositions to be prepared which exhibit advantageous self-bleed properties after post-bake. At low viscosities, the fluid is useful as an additive for personal care products and enables such products to exhibit water and oil repellency as well as a resistance to wash off.

According to the present invention, methyl-phenyl-containing fluorosilicone terpolymeric fluids over the viscosity range of 16,000 cps to 200,000 cps (16M to 200M cps) are used in fluorosilicone-containing heat curable rubber compositions to promote a finger transferrable bleed after post bake. The higher viscosity fluids are used in the manufacture of gaskets, seals, pulsator parts and dampening agents. The higher viscosity phenyl-containing fluorosilicone terpolymeric fluids of the present invention are useful in a wide variety of fluorosilicone heat curable rubber compositions. The lower viscosity fluids in the range of from 30 to 1,000 cps are particularly useful in personal care and cosmetic applications such as skin lotions, cosmetic creams, suntan lotions, hair conditioners, hair sprays, antiperspirants, deodorants and lipsticks.

According to the present invention, methyl- and phenyl-containing fluorosilicone terpolymeric fluids over the viscosity range of 1,000 cps to 16,000 cps are useful as plasticizing fluids to soften and enhance low temperature performance of fluorosilicones and fluorosilicone-fluorohydrocarbon blends. These intermediate viscosity fluids reduce the low temperature brittle point of these compositions rendering them useful over a broader temperature range.

The self-bleed additives of the present invention can be used in a wide variety of fluorosilicone compositions, fluorosilicone copolymers, fluorosilicone terpolymers, and other fluorosilicone blends. The fluorosilicones in which the self-bleed additives can be used may include both low and high molecular weight fluorosilicone fluids and gums having a fluorine content of up to 37 percent by weight. It is expected that the self-bleed additives are even useful in fluorosilicones having greater than 37 percent fluorine by weight, although such fluorosilicones are usually not practicable.

The self-bleed additives of the present invention provide fluorosilicone HCR compounds which self-bleed both during press cure and during post bake. The noncompatible self-bleed additives provide a self-bleed property without significantly affecting the physical properties of the composition. In addition, the present invention provides self-bleed additives which do not liberate excess volatiles in the post-bake oven.

The present invention also provides a process for reacting three cyclic silicone oligomers by ring opening polymerization to form the terpolymeric fluid additives of the present invention. To promote the ring opening polymerization, a small Mount of polyethylene glycol or methoxy-terminated polyethyleneglycol is added to the reaction vessel. The mixture is then catalyzed, preferably with potassium silanolate, to effect the ring opening polymerization.

DETAILED DESCRIPTION OF THE INVENTION

According to the present invention, methyl- and phenyl-containing fluorosilicone terpolymeric fluids having viscosities in the range of from 30 cps to 200M cps are used as additives for various applications. The additives of the present invention are comprised of the reaction product from three cyclic silicone oligomers which have preferably been reacted with an M-type chain stopper. The three cyclics are reacted together by a ring opening process. The ring opening process is promoted by the addition of either polyethyleneglycol or methoxy-terminated polyethyleneglycol. The mixture is then catalyzed with potassium silanolate or lithium hydroxide. The high viscosity additives are only marginally compatible with the fluorosilicone compound to which they are added.

A chain stopper of the M-type is preferred, particularly for the self-bleed additive applications. Reactive end groups such as vinyl and silanol are more likely to be compatible and react with the fluorosilicone HMW composition when cured. If compatible, the resulting compositions typically do not exhibit self-bleed properties. If the self-bleed additive does have a reactive end group, the additive can still be used, however, it will now serve in the role of a curable plasticizer.

The additives of the present invention, whether in the form of a self-bleed additive, a personal care product additive, or a plasticizing additive, comprise the reaction product of (A) a fluorosilicone cyclic oligomer, (B) a methylsiloxane cyclic oligomer, (C) a phenylsiloxane cyclic oligomer, and (D) a chain stopper. In one embodiment component (A) is a fluorosilicone cyclic trimer, for instance, 3,3,3,-trifluoropropyl-methylsiloxane cyclic trimer. In one embodiment component (B) is dimethylsiloxane cyclic tetramer. In one embodiment component (C) is diphenylsiloxane cyclic tetramer. In one embodiment component (D) is an M-stopped siloxane having between 1 and 30 siloxane units. In another embodiment component (D) is a vinyl-terminated chain stopper having between 1 and about 30 siloxane units.

The additives cover a wide range of viscosities and are preferred over the range of from 30 cps to 200M cps at 25° C. The lower viscosity fluids in the range of from 30 to 1,000 cps are particularly useful in personal care and cosmetic applications. The intermediate viscosity fluids in the range of from about 1,000 to about 16,000 cps are useful as plasticizing additives to soften and enhance the low temperature performance of fluorosilicones and blends of fluorosilicones and fluorohydrocarbons. The plasticizing additive fluids reduce the low temperature brittle point of these compositions rendering them useful over a wider temperature range. The higher viscosity fluids in the range of from about 16M to about 200M are used in fluorosilicone rubber compositions for the manufacture of gaskets, seals, pulsator parts and dampening agents. One particularly useful range for the manufacture of gaskets, seals, pulsator parts and dampening agents is from 80M to 90M cps at 25° C.

When used as a self-bleed additive, the amount of self-bleed additive required to effect a finger transferable bleed varies over the range of 6 to 15 parts by weight based on 100 parts by weight of fluorosilicone HCR composition. More preferably, the self-bleed additive is used over the range of 8 to 12 parts by weight based on 100 parts by weight of fluorosilicone HCR composition. The range of between 8 and 10 parts by weight is most preferred. The amount of self-bleed additive should be kept below 15 parts by weight because higher levels tend to affect processability, shrinkage and the physical property profile.

The fluorosilicone heat curable rubber compositions to which the self-bleed additives of the present invention may be added include those fluorosilicone HCR compounds which, when catalyzed, produce cured compositions having a shore A durometer measurement of between 18 and 80. Preferred fluorosilicone HCR compositions have a durometer in the cured state of between 20 and 30 in the cured state. Many gasket and sealing applications require a fluorosilicone HCR composition having a durometer of about 25 in the cured state.

For personal care and cosmetic additive applications, it is preferred that the fluid has a viscosity of between about 30 and 1,000 cps at 25° C. When used as an additive for personal care and cosmetic products, the low viscosity fluid of the present invention is preferably used in an amount of between about 0.001 and 0.1 percent by weight. The additive may be used in a greater amount, for example, up to 1.0 percent by weight or higher, but typically provides the desired properties at the lower range of weight percentage.

The intermediate viscosity fluids having a viscosity over the range of 1,000 cps to 16,000 cps are preferably used in an amount of between about 0.5 and about 20 parts by weight based on 100 parts of base silicone composition to which they are added. Preferably, the plasticizing additives of the present invention are used to enhance the low temperature performance of fluorosilicones and fluorosilicone-fluorohydrocarbon blends which have shore A durometers over the range of 60 to about 90, and fluorine contents over the range of about 50% and about 65%.

The type of self-bleed resulting from compositions incorporating the high viscosity additives is such that, when handled, a user can feel that there is a lubricant on the surface of a molded part and some of the lubricant is transferred to the user's hands.

No raw fumed silica has to be added to soak up the fluid from the composition. The present invention does not require additional fumed silica to improve incorporation of the self-bleed additive or the processability of the desired composition.

The present invention also relates to a process for manufacturing the additives of the present invention. The process comprises a ring opening polymerization of three cyclic silicone oligomers to form a methyl- and phenyl-containing fluorosilicone terpolymeric fluid additive. The process generates a very small amount of cyclics. When forming high viscosity fluids, the process results in a self-bleed additive which exhibits a very low level of excess volatiles during post bake, and which exhibits self-bleed after post bake. The ring opening process forms a block-terpolymer having a substantially homogeneous distribution of the individual oligomeric moieties as opposed to a random tiered structure which results from a condensation reaction. Also, unlike a condensation reaction, the present invention does not require the use of starting hydrolyzates which are devoid of any cyclic species.

To promote the ring opening polymerization process, a small amount of either polyethyleneglycol or methoxypolyethyleneglycol (methoxy-terminated polyethyleneglycol) promoter is added to the mixture of the three cyclic oligomers and M-stopper. An amount within the range of 0.008 to 0.01 percent by weight may be preferred for some applications. The promoter enables the cyclic oligomers to have much more reactive ring structures. The use of a promoter enables the rings to open up at much lower temperatures. The promoter also propagates a kinetic rate of polymerization. The use of methoxy-terminated polyethyleneglycol promoter in combination with a potassium silanolate catalyst has found to significantly facilitate the ring opening polymerization process.

While potassium silanolate is preferably the catalyst used to open the rings, sodium hydroxide, lithium hydroxide and cesium hydroxide and their silanolate analogues may also be used. These various catalyzing agents have different relative reactivities with respect to the present polymerization—compensation must be made accordingly for these. When either the polyethyleneglycol or methoxypolyethyleneglycol promoter is added to the reaction vessel along with potassium silanolate catalyst, the promoter forms a very reactive cation complex with the potassium silanolate. The reactive cation complex facilitates the ring opening of the cyclics and thus, facilitates the ring opening polymerization.

Table 1 below shows the results of tests conducted on control compositions and compositions having fluorosilicone terpolymeric fluid additives according to the present invention. Additives having viscosities of 16M, 86M and 146M cps at 25° C. (Examples F–K), were tested. All of the terpolymer fluids were found to self-bleed after press-cure and post-bake. The 16M cps fluid had a greater effect upon the percentage of linear shrinkage while the 146M fluid had a tendency to be somewhat sticky on the mill.

As shown in Table 2 below, one embodiment of the invention relates to the use of additive over the range of 8–10 parts by weight based on 100 parts by weight fluorosilicone HMW composition. The range of 8–10 parts by weight is particularly preferred when the additive is a phenyl-containing fluorosilicone terpolymertc fluid having a viscosity of between about 80M and about 90M. At this amount and viscosity, the self-bleed additive has a minimal effect upon processability and physical properties.

The terpolymeric fluids are prepared according to a method of the present invention whereby various cyclic reactants selected from cyclic oligomers are catalyzed through a ring opening polymerization step which uses potassium silanolate and a polyethyleneglycol promoter. The potassium silanolate catalyst and the promoter are disclosed in U.S. Pat. Nos. 4,122,247 and 4,157,337, both to E. R. Evans, which are herein incorporated by reference. The promoter serves to effect a more equivalent rate of opening the rings of the disparate oligomers. The promoter helps the formation of a more alternating type structure and provides a fluid product which has a low level of cyclics (<5.0%).

The potassium silanolate preferably has a KOH equivalent weight of about 5 percent and is added in an amount of about 0.033 parts by weight based on 100 parts by weight of cyclic oligomer.

The procedure is effective for the preparation of either a trimethylsilyl or a vinyldimethylsilyl terminated fluid.

The fluids according to the present invention have a phenyl-containing oligomer component over the range of 20 to 60 weight percent, a fluorosilicone-containing oligomer component over the range of 10 to 40 weight percent, and a methyl-containing oligomer component over the range of 20 to 50 weight percent. Some preferred fluids according to the invention have a phenyl-containing oligomer component over the range of 30–48 weight percent, a fluorosilicone-containing oligomer component over the range of 14–20 weight percent, and a dimethyl-containing oligomer component over the range of 30–40 weight percent.

The chainstopper is preferably used over the range of 0.28 to 31.0 percent by weight.

The specific examples below illustrate methods of producing the self-bleed fluids of the invention.

The fluorosilicone heat curable rubber composition which was used in each of examples A–K shown in table 2 below and labelled "compound", is described below. The fluorosilicone HCR composition (compound) had the following components:

Component A—60 parts by weight high molecular weight straight fluorosilicone gum having vinyl end stops and 0.07 percent by weight vinyl-on-chain;

Component B—40 parts by weight high molecular weight straight fluorosilicone gum having vinyl end stops and no vinyl-on-chain;

Component C—5.5 parts by weight copolymer formed of polydimethylsiloxane and M-stopped vinylmethyldisiloxy and having between 4 and 4.4 percent by weight vinyl-on-chain;

Component D—1 part by weight vinyl terminated polydimethylsiloxane fluid having a viscosity of between 450,000 and 525,000 centipoise at 25° C;

Component E—5.8 parts by weight fluorosilicone disiloxanol telomeric fluid having a silanol content over the range of 6.2 to 6.9 weight percent and a viscosity over the range of 60 to 90 centipoise;

Component F—0.05 part by weight iron octoate heat age additive;

Component G—0.25 part by weight fumed titanium dioxide in the form of $TiO_2$ (P25); and Component H—16 parts by weight fumed silica having an average particle size of 225 $m^2/gm$.

While the above fluorosilicone HCR composition is only exemplary, it is to be understood that the self-bleed additives of the present invention may be added to a wide variety of fluorosilicone HCR compositions to provide cured products which exhibit a self-bleed after post-baking. In particular, fluorosilicone HCR compositions are preferred which are similar to the composition used in the examples below but which have an amount of fumed silica over the range of 10 to 40 parts by weight based on 100 parts by weight of the fluorosilicone components in the composition. Preferably, the fluorosilicone HCR compositions to which the self-bleed additive may be added are high molecular weight fluorosilicone gums or blends of high molecular weight fluorosilicone gums. The amount of other additives blended with the high molecular weight fluorosilicone gum is dependent upon the desired viscosity of the uncured composition application of the cured product.

EXAMPLE I

To a polymerization vessel is added 248.0 grams of 3,3,3-trifluoroproplymethylsiloxane cyclic trimer, 06.0 grams of dimethylsiloxane cyclic tetramer, 762 grams of diphenylsiloxane cyclic tetramer and 20.2 grams of an M-type chain stopper having the formula:

The mixture was thoroughly agitated while under a blanket of nitrogen before adding 0.14 grams of methoxy-terminated polyethyleneglycol available as Carbowax 550 from Union Carbide. The Carbowax has a molecular weight of 525–575 and a specific gravity of 1,089 at 20° C.

The mixture was heated to 145° C. where 0.4 ml of potassium silanolate (4.9 weight percent KOH equivalent) was added and the agitation rate was increased during the exothermic reaction. After the exotherm (5° C. rise) started to subside, the temperature was raised to 155° C. and held at 155° C. for 10 hours. The catalyst was neutralized via the addition of 0.32 grams of silylphosphate (equivalent to 12 percent $H_3PO_4$). The clear fluid had a volatiles content of 3.9 weight percent. The recovered yield was 1,610 grams. The material had a specific gravity of 1.1247 at 27° C. and a refractive index of 1.5037 $n^D$ at 25° C. The viscosity of the fluid was 33,000 cps at 25° C.

The method in Example I was repeated using different amounts of the cyclics and chain-stopper to form the viscosity fluids shown in Table 1 below.

TABLE 1

| M-Stopped Terpolymer Fluids | | | |
|---|---|---|---|
| Viscosity cps/25° C. | 86,000 | 16,320 | 144,000 |
| Volatiles % | 4.5 | 4.7 | 4.2 |
| & Yield | 88.39 | — | 96.0 |

EXAMPLE II

A vinyl terminated version of the terpolymer fluid was prepared in a similar manner. Fluorosilicone cyclic trimer (124.0 grams), octamethylcyclotetrasiloxane (303 grams) and 381 grams of diphenylsiloxane cyclic tetramer were placed in a reaction vessel. To the mixture was added 0.07 grams of Carbowax 550 and 50 grams of the vinyl terminated chain stopper

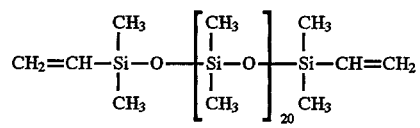

The mixture was heated to 145° C. then catalyzed with 0.2 grams of potassium silanolate. The reaction parameters were the same as described in Example 1, and the catalyst was neutralized with silylphosphate to provide a fluid with a volatiles content of 3.5 weight percent. The fluid was vacuum stripped at 160° C. to provide a material with a volatiles content of 1.2 weight percent and a viscosity of 29,100 cps at 25° C. The SpG was 1,123 g/cc at 25° C. and the vinyl content was 0.44 weight percent by chemical titration.

The M-stopped terpolymeric fluids were effective in providing a self bleed both after press-cure and post-bake as shown in Table 2. Compounds F through K were fully effective whereas compounds B through E, which include phenyl-containing copolymeric fluids, displayed bleeding only after press cure and note after post bake. As shown in Table 2, the range of 8–10 parts by weight has the least effect upon processability and physical properties. Also, the fabricator prefers a self-bleed additive which will not liberate excess volatiles in the post-bake oven as was observed with compound B. The compounds containing the terpolymeric fluid lost from 5.0 to 6.3 weight percent during the post bake.

One preferred fluid has a viscosity of from 80M to 90M cps at 25° C. because it has minimal effect on physical properties, has little effect on processability, and has less than a 6.0 percent weight loss on post baking. Unlike the phenyl-containing copolymeric fluids, the terpolymeric fluids do not liver-up the stock while on the mill and do not require additional fumed silica for incorporation and processability. Also, unlike the compositions described by Yoshida, no diphenyldiol is used as a filler-treating agent.

TABLE 2-A

| | FLUOROSILICONE HCR COMPOUND | | | | | |
|---|---|---|---|---|---|---|
| | A | B | C | D | E | F |
| Compound[1] | 100 | 100 | 100 | 100 | 100 | 100 |
| [M-stopped fluid][2] | — | 5.1 | — | — | — | — |
| [DMDPH][3] | — | — | 10 | — | — | — |
| Phenyl Fluid[4] | — | 2.5 | 10 | 4.0 | 6.0 | — |
| Fluid 16M | — | — | — | — | — | — |
| Fluid 86M | — | — | — | — | — | 9.0 |
| Fluid 146M | — | — | — | — | — | — |
| Fumed Silica | — | 1.0 | 2.0 | 2.0 | 3.0 | — |
| Luperco 101XL | 1.0 | 1.0 | 1.1 | 1.04 | 1.06 | 1.04 |
| Post-bake 15'/350° F. and press-cure 4 hrs/400° F. PHYSICAL PROPERTIES | | | | | | |
| Shore A | 29 | 22 | 28 | 27 | 26 | 21 |
| 100% Modulus | 83 | 65 | 67 | 61 | 61 | 62 |
| Tensile, psi | 1150 | 1113 | 976 | 1063 | 1051 | 938 |
| Elongation, % | 570 | 619 | 632 | 665 | 681 | 624 |
| Die B Tear | 78 | 88 | 112 | 106 | 95 | 77 |
| SpG | 1.370 | 1.368 | 1.362 | 1.370 | 1.362 | 1.340 |
| % Wgt. Loss | — | — | — | — | — | 5.8 |
| Press-cure Bleed | No | + | + | + | ++ | +++ |
| Post-bake Bleed | No | No | No | No | No | + |
| Processability | Good | Good | Good | Good | Good | Good |

| Linear Shrinkage Percentage | Length | Width |
|---|---|---|
| Press-cure | 3.10 | 2.84 |
| Post-bake | 4.65 | 3.62 |

[1]Previously identified
[2]100 cps M[SiO]$_x$M fluid where x = 30
[3]An M-stopped (trimesthylsilyl) diphenyldimethylpolysiloxane having a phenyl content of 65 percent by weight. The fluid has a viscosity specification range of 200–5000 cps but the average value is over the range of 230–300 cps at 25° C.
[4]A methoxy terminated diphenylsiloxy-dimethylsiloxy copolymeric fluid. The fluid has a weight percent methoxy content over the range of 6.4–8.5. The fluid has a viscosity of 32–60 centistokes and a phenyl content over the range of 50–55 percent and a Me$_2$SiO content of 38–43 percent. A fluid with 7 weight percent methoxy has the structure: $(CH_3)_2(CH_3O)SiO[(C_6H_5)_2SiO]_2[(CH_3)_2SiO]_4OSi(OCH_3)(CH_3)_2$.

TABLE 2-B

| | FLUOROSILICONE HCR COMPOUND | | | | |
|---|---|---|---|---|---|
| | G | H | I | J | K |
| Compound[1] | 100 | 100 | 100 | 100 | 100 |
| [M-stopped fluid][2] | — | — | — | — | — |
| [DMDPh][3] | — | — | — | — | — |
| Phenyl Fluid[4] | — | — | — | — | — |
| Fluid 16M | — | — | 8 | 9 | 10 |
| Fluid 86M | — | — | — | — | — |
| Fluid 146M | 8 | 10 | — | — | — |
| Fumed Silica | — | — | — | — | — |
| Luperco 101XL | 1.08 | 1.1 | 1.08 | 1.1 | 1.1 |
| Post-bake 15'/350° F. and press-cure 4 hrs/400° F. PHYSICAL PROPERTIES | | | | | |
| Shore A | 22 | 21 | 21 | 22 | 21 |
| 100% Modulus | 52 | 50 | 56 | 65 | 51 |
| Tensile, psi | 977 | 980 | 964 | 867 | 944 |
| Elongation, % | 630 | 633 | 623 | 606 | 631 |
| Die B Tear | 73 | 75 | 77 | 75 | 78 |
| SpG | 1.348 | 1.341 | 1.345 | 1.388 | 1.340 |
| % Wgt. Loss | 5.2 | 6.0 | 5.9 | 5.9 | 6.1 |
| Press-cure Bleed | +++ | +++ | +++ | +++ | +++ |
| Post-bake Bleed | + | + | + | + | + |
| Processability | Slightly Sticky | Slightly Sticky | Good | Good | Good |

TABLE 2-B-continued

| Linear Shrinkage Percentage | Length | Width |
| --- | --- | --- |
| Press-cure | 3.58 | 3.0 |
| Post-bake | 5.48 | 3.28 |

[1]Previously identified
[2]100 cps M[SiO]$_x$M fluid where x = 30
[3]An M-stopped (trimesthylsilyl) diphenyldimethylpolysiloxane having a phenyl content of 65 percent by weight. The fluid has a viscosity specification range of 200–5000 cps but the average value is over the range of 230–300 cps at 25° C.
[4]A methoxy terminated diphenylsiloxy-dimethylsiloxy copolymeric fluid. The fluid has a weight percent methoxy content over the range of 6.4–8.5. The fluid has a viscosity of 32–60 centistokes and a phenyl content over the range of 50–55 percent and a Me$_2$SiO content of 38–43 percent. A fluid with 7 weight percent methoxy has the structure: $(CH_3)_2(CH_3O)SiO[(C_6H_5)_2SiO]_2[(CH_3)_2SiO]_4OSi(OCH_3)(CH_3)_2$.

In another embodiment, the present invention relates to the use of low viscosity, phenyl-containing fluorosilicone terpolymeric fluids for personal care applications. The range of viscosities useful for this application is from 30 cps to 1,000 cps at 25° C. Examples III and IV below describe the synthesis of low viscosity self-bleed additive fluids.

EXAMPLE III

The same methyl-3,3,3-trifluoropropylmethylsiloxane cyclic trimer, dimethylsiloxane cyclic tetramer, and chain modifier $(CH_3)_3Si—O—[Si(CH_3)_2—O—]Si(CH_3)_3$ used in were dried via elution through No. 8 mesh indicating silica gel. The diphenylsiloxane cyclic tetramer being crystalline, was used as is.

To a clean polymerization flask was charged 350 grams of fluorosilicone cyclic trimer, 733 grams of dimethylsiloxane cyclic tetramer, 952 grams of diphenylsiloxane cyclic tetramer and 0.30 grams of Carbowax 550. The contents of the flask were agitated while sparging with nitrogen. The vessel was heated to 130–135° C. where the nitrogen mode was switched to blanket and the rate was reduced. The chain stopper, 260.4 grams, was added and after a brief agitation the catalyst, 0.51 grams of potassium silanolate (4.9% KOH equivalent), was added. The polymerization displayed an exotherm of 4° C. and the temperature was increased to 159° C. The 159° C. temperature was held for 10 hours before a sufficient amount of silylphosphate (equivalent to 12% HA$_3$PO$_4$) was added to neutralize the catalyst. A clear fluid weighing 2266 grams was recovered which had a volatiles content of 5.7 weight percent.

The fluid (1276 grams) was vacuum stripped at 37 mm and 240° C. to provide 1198 grams of a fluid with a volatiles content of 1.7 weight percent. The recovered yield was 93.9%. The final viscosity was 380 cps at 25° C. and the specific gravity was 1.0941 at 27° C. The refractive index of the fluid was 1.4845 at 26° C.

EXAMPLE IV

As in Example III, the designated cyclic oligomers and chain stopper were pre-dried prior to polymerization.

To a clean polymerization flask was charged 361 grams of fluorosilicone cyclic trimer, 247 grams of dimethylsiloxane cyclic tetramer, 960 grams of diphenylsiloxane cyclic tetramer, 705 grams of chain stopper (MD$_2$M) and 0.28 grams of Carbowax 550. The system was heated to 130°–135° C. while sparging with nitrogen. Holding this temperature, the nitrogen mode was changed to blanket and the rate of nitrogen entering the system decreased. The catalyst, 0.48 grams of potassium silanolate (4.9% KOH equivalent), was added and the reaction displayed an exotherm of 4° C. The temperature was then increased to 160° C. and held for 10 hours prior to the neutralization with 0.65 grams of silylphosphate. A clear fluid weighing 2261 grams was recovered which had a volatiles content of 23% and a viscosity of 34 cps at 25° C. The recovered yield was 99%. Vacuum stripping of 1272 grams at 35mm vacuum and 250° C. provided 973.5 grams (76.5% yield) of a fluid with a volatiles level of 2.5% and a viscosity of 234 cps at 25° C. The specific gravity was 1.1140 at 24° C. and the refractive index was 1.5031 at 22° C.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed:

1. A method of producing a phenol-containing block terpolymeric fluorosilicone fluid, said process comprising the steps of:

mixing together in a reaction vessel (A) a fluorosilicone cyclic oligomer, (B) a methylsiloxane cyclic oligomer, (C) a phenylsiloxane cyclic oligomer, and (D) a chain stopper to form a mixture of cyclic oligomers;

mixing said mixture of cyclic oligomers with a catalytic amount of ring opening catalyst;

mixing said mixture of cyclic oligomers with a promoter, wherein said promoter is at least one member selected from the group consisting of polyethylene glycol and methoxy-terminated polyethyleneglycol; and allowing the mixture to react in the presence of said catalyst at a temperature ranging form about 130° C. to about 160° C. for a period of time of about at least ten hours to form a phenol-containing fluorosilicone terpolymeric fluid;

whereby said terpolymeric fluid has a volatiles content of less than 5.0 weight percent, a viscosity ranging from 30 centipoise to 200M centipoise at 25° C. and a substantially homogeneous distribution of the said individual oligomers in said block terpolymer.

2. A method as in claim 1, wherein said ring opening catalyst is potassium silanolate.

3. A method as in claim 1, further comprising the step of neutralizing the catalyst with a neutralizing agent.

* * * * *